(12) United States Patent
Kim et al.

(10) Patent No.: US 10,786,667 B1
(45) Date of Patent: Sep. 29, 2020

(54) METHOD OF USING MULTICHANNEL STIMULATION SYSTEM FOR REGENERATING DAMAGED CORNEAL NERVES

(71) Applicant: NU EYNE CO., LTD., Seoul (KR)

(72) Inventors: Do-Hyoung Kim, Seoul (KR); Pyung-Kyu Kim, Seoul (KR); Joo-Wan Seo, Seoul (KR); Won-Jang Lee, Daejeon (KR)

(73) Assignee: NU EYNE CO., LTD., Seoul (KR)

( * ) Notice: Subject to any disclaimer, the term of this patent is extended or adjusted under 35 U.S.C. 154(b) by 0 days.

(21) Appl. No.: 16/742,167

(22) Filed: Jan. 14, 2020

(30) Foreign Application Priority Data

Apr. 16, 2019 (KR) .......................... 10-2019-0044506

(51) Int. Cl.
*A61N 1/04* (2006.01)
*A61N 1/36* (2006.01)

(52) U.S. Cl.
CPC ....... *A61N 1/0464* (2013.01); *A61N 1/36034* (2017.08); *A61N 1/36046* (2013.01)

(58) Field of Classification Search
CPC .. A61N 1/0456; A61N 1/0464; A61N 1/0543; A61N 1/36034; A61N 1/36046
See application file for complete search history.

(56) References Cited

U.S. PATENT DOCUMENTS

| | | | |
|---|---|---|---|
| 2011/0196353 A1* | 8/2011 | DeLand | A61N 5/0616 606/9 |
| 2014/0330336 A1* | 11/2014 | Errico | A61N 1/3603 607/45 |
| 2015/0057701 A1* | 2/2015 | Kelleher | A61H 23/0236 606/204.15 |
| 2016/0106576 A1* | 4/2016 | Badawi | A61K 8/0208 607/109 |
| 2017/0224990 A1* | 8/2017 | Goldwasser | A61N 1/36014 |
| 2018/0001108 A1* | 1/2018 | Kelleher | A61N 5/0617 |
| 2019/0143116 A1* | 5/2019 | Mowery | A61N 1/0456 607/53 |
| 2019/0217094 A1* | 7/2019 | Claude | A61N 1/36021 |
| 2019/0336765 A1* | 11/2019 | Charlesworth | A61N 1/36 |

FOREIGN PATENT DOCUMENTS

KR 20180125997 11/2018

* cited by examiner

*Primary Examiner* — Eric D. Bertram
(74) *Attorney, Agent, or Firm* — IPLA P.A.; James E. Bame

(57) ABSTRACT

A multichannel stimulation system for regenerating damaged corneal nerves, includes: electrically contacting a contactor of the multichannel unit with the stimulation signal module; providing an electric pulse signal, by the stimulation signal module; transferring an electric pulse signal of a first duration time and an electric pulse signal of a seventh duration time to the first channel, and transferring an electric pulse signal; maintaining an adjusted magnitude of the absolute value of an electric pulse signal when the magnitude of the absolute value of the electric pulse signal desired by a user is adjusted; and confirming whether impedance measured between the first channel and an area where the first channel is attached and impedance measured between the second channel and an area where the second channel is attached exceed a reference impedance.

16 Claims, 8 Drawing Sheets

METHOD OF USING MULTICHANNEL STIMULATION SYSTEM FOR REGENERATING DAMAGED CORNEAL NERVES

CROSS REFERENCE

The present application claims priority to Korean Patent Application No. 10-2019-0044506, filed 16 Apr. 2019, the entire contents of which is incorporated herein by its entirety.

BACKGROUND

The present invention relates to a method of using a multichannel stimulation system for regenerating damaged corneal nerves, and more specifically, to a method of using a multichannel stimulation system for regenerating damaged corneal nerves, which can effectively transfer an electric pulse signal into multiple channel attaching areas by applying the electric pulse signal as a stimulation signal through multiple channels attached in a plurality of areas close to the eyes, and measuring impedance between the multiple channels and the multiple channel attaching areas.

After the permission of Food and Drug Administration (FDA) in the mid-1990s, about 30 million people worldwide have undergone vision correction surgery for myopia treatment, and recently in Korea, more than half of the population needs vision correction surgery as a result of aging population and rapid increase in the use of digital devices.

Accordingly, it is estimated that more than 200,000 people undergo laser vision correction surgery every year in Korea, and this laser vision correction surgery damages the corneal nerve bundles in the process of physically affecting the corneal epithelium to correct refractive error.

The density and sensory function of the actual corneal nerve bundles tend to decrease immediately after the laser vision correction surgery, and it has been found that dry eye syndrome and corneal pain, which are frequent side effects of the laser vision correction surgery, are closely related to the corneal nerve bundles.

Recently, thanks to the rapid development of neuromodulation and research of nervous system, understanding of the growth and function of nerve cells is increasing. In addition, according to the accumulated technologies, it is shown that nerve regeneration may control activities by means of inherent features and regeneration of nerves and tissues can be accelerated by using minute electrical stimulation in regenerating peripheral nerves.

Accordingly, although various methods are proposed to treat patients suffering from visual disorder using minute electrical stimulation, effective treatment is difficult as the methods simply exercise electrical stimulation through probes.

The background technology of the present invention is disclosed in Korean Laid-opened Patent No. 10-2018-0125997 released on Nov. 26, 2018.

SUMMARY OF THE INVENTION

Therefore, the present invention has been made in view of the above problems, and it is an object of the present invention to provide a method of using a multichannel stimulation system for regenerating damaged corneal nerves, which can effectively transfer an electric pulse signal into multiple channel attaching areas by applying the electric pulse signal as a stimulation signal through multiple channels attached in a plurality of areas close to the eyes, and measuring impedance between the multiple channels and the multiple channel attaching areas.

The technical problems to be solved by the present invention are not limited to the technical problems mentioned above, and unmentioned other technical problems may be clearly understood by those skilled in the art from the following descriptions.

To accomplish the above object, according to one aspect of the present invention, there is provided a method of using a multichannel stimulation system for regenerating damaged corneal nerves, the system comprising: a multichannel unit including a first channel formed of a conductive material and attached between an area above the left eye and the left eyebrow to transfer a stimulation signal, and a second channel formed of a conductive material, attached between an area above the right eye and the right eyebrow to transfer the stimulation signal, and formed in one piece together with the first channel; and a stimulation signal module for providing the first channel and the second channel with an electric pulse signal as the stimulation signal, and the method comprising the steps of: providing the electric pulse signal configured of a positive current electric pulse signal during a first duration time, a zero current electric pulse signal during a second duration time following the first duration time, a negative current electric pulse signal during a third duration time following the second duration time, a zero current electric pulse signal during a fourth duration time following the third duration time, a negative current electric pulse signal during a fifth duration time following the fourth duration time, a zero current electric pulse signal during a sixth duration time following the fifth duration time, a positive current electric pulse signal during a seventh duration time following the sixth duration time, and a zero current electric pulse signal during an eighth duration time following the seventh duration time, by the stimulation signal module; transferring the electric pulse signal of the first duration time and the electric pulse signal of the seventh duration time to the first channel, and transferring the electric pulse signal of the third duration time and the electric pulse signal of the fifth duration time to the second channel, by the stimulation signal module; maintaining an adjusted magnitude of the absolute value of the electric pulse signal, when the magnitude of the absolute value of the electric pulse signal desired by a user is adjusted by controlling to increase the magnitude of the absolute value of the electric pulse signal in proportion to the number of times of applying a pressure to an up button of the stimulation signal module and controlling to decrease the magnitude of the absolute value of the electric pulse signal in inverse proportion to the number of times of applying a pressure to a down button of the stimulation signal module; and measuring impedance between the first channel and an area where the first channel is attached and impedance between the second channel and an area where the second channel is attached, and confirming whether the impedance measured between the first channel and the area where the first channel is attached and the impedance measured between the second channel and the area where the second channel is attached exceed a reference impedance, wherein the length of the first duration time of the electric pulse signal is 2 to 15 times of the length of the third duration time of the electric pulse signal, and the length of the fifth duration time of the electric pulse signal is 2 to 15 times of the length of the seventh duration time of the electric pulse signal.

In the method of using a multichannel stimulation system for regenerating damaged corneal nerves, at the step of confirming whether the reference impedance is exceeded, the stimulation signal module may apply a DC voltage of a predetermined amplitude to the first channel, measure a current between the first channel, the area where the first channel is attached, the area where the second channel is attached, and the second channel, and confirm that the impedance exceeds the reference impedance when the measured current is lower than a threshold value.

In the method of using a multichannel stimulation system for regenerating damaged corneal nerves, at the step of confirming whether the reference impedance is exceeded, if it is confirmed that the impedance exceeds the reference impedance, the stimulation signal module may stop supply of the current of the electric pulse signal of the adjusted magnitude of the absolute value.

In the method of using a multichannel stimulation system for regenerating damaged corneal nerves, at the step of confirming whether the reference impedance is exceeded, if it is confirmed that the current measured between the first channel, the area where the first channel is attached, the area where the second channel is attached, and the second channel is higher than the threshold value and thus the impedance does not exceed the reference impedance, the stimulation signal module may provide the first channel and the second channel with the electric pulse signal of the adjusted magnitude of the absolute value.

In the method of using a multichannel stimulation system for regenerating damaged corneal nerves, magnitude of the absolute value of the positive current electric pulse signal of the first duration time of the electric pulse signal may be equal to magnitude of the absolute value of the negative current electric pulse signal of the third duration time of the electric pulse signal, and magnitude of the absolute value of the negative current electric pulse signal of the fifth duration time of the electric pulse signal may be equal to magnitude of the absolute value of the positive current electric pulse signal of the seventh duration time of the electric pulse signal.

In the method of using a multichannel stimulation system for regenerating damaged corneal nerves, magnitude of the absolute value of the positive current electric pulse signal of the first duration time of the electric pulse signal may be 2 to 15 times of magnitude of the absolute value of the negative current electric pulse signal of the third duration time of the electric pulse signal, and magnitude of the absolute value of the negative current electric pulse signal of the fifth duration time of the electric pulse signal may be 2 to 15 times of magnitude of the absolute value of the positive current electric pulse signal of the seventh duration time of the electric pulse signal.

In the method of using a multichannel stimulation system for regenerating damaged corneal nerves, the electric pulse signal may be in a charge-balanced state.

To accomplish the above object, according to another aspect of the present invention, there is provided a method of using a multichannel stimulation system for regenerating damaged corneal nerves, the system comprising: a multichannel unit including a 11-th channel formed of a conductive material and attached above the left eyebrow to transfer a stimulation signal, a 12-th channel formed of a conductive material and attached below the left eye to transfer the stimulation signal, a 21-th channel formed of a conductive material and attached above the right eyebrow to transfer the stimulation signal, and a 22-th channel formed of a conductive material, attached below the right eye to transfer the stimulation signal, and formed in one piece together with the 11-th channel, the 12-th channel and the 21-th channel; and a stimulation signal module for providing the 11-th channel, the 12-th channel, the 21-th channel and the 22-th channel with an electric pulse signal as the stimulation signal, and the method comprising the steps of: providing the electric pulse signal configured of a positive current pulse signal during a first duration time, a zero current electric pulse signal during a second duration time following the first duration time, a negative current pulse signal during a third duration time following the second duration time, a zero current electric pulse signal during a fourth duration time following the third duration time, a negative current pulse signal during a fifth duration time following the fourth duration time, a zero current electric pulse signal during a sixth duration time following the fifth duration time, an electric pulse signal during a seventh duration time following the sixth duration time, and a zero current electric pulse signal during an eighth duration time following the seventh duration time, by the stimulation signal module; transferring the electric pulse signal of the first duration time and the electric pulse signal of the seventh duration time to the 11-th channel, transferring the electric pulse signal of the third duration time and the electric pulse signal of the fifth duration time to the 12-th channel, transferring the electric pulse signal of the first duration time and the electric pulse signal of the seventh duration time to the 21-th channel, and transferring the electric pulse signal of the third duration time and the electric pulse signal of the fifth duration time to the 22-th channel, by the stimulation signal module; maintaining an adjusted magnitude of the absolute value of the electric pulse signal, when the magnitude of the absolute value of the electric pulse signal desired by a user is adjusted by controlling to increase the magnitude of the absolute value of the electric pulse signal in proportion to the number of times of applying a pressure to an up button of the stimulation signal module and controlling to decrease the magnitude of the absolute value of the electric pulse signal in inverse proportion to the number of times of applying a pressure to a down button of the stimulation signal module; and measuring impedance between the 11-th channel and an area where the 11-th channel is attached and impedance between the 12-th channel and an area where the 12-th channel is attached, measuring impedance between the 21-th channel and an area where the 21-th channel is attached and impedance between the 22-th channel and an area where the 22-th channel is attached, confirming whether the impedance measured between the 11-th channel and the area where the 11-th channel is attached and the impedance measured between the 12-th channel and the area where the 12-th channel is attached exceed a reference impedance, and confirming whether the impedance measured between the 21-th channel and the area where the 21-th channel is attached and the impedance measured between the 22-th channel and the area where the 22-th channel is attached exceed a reference impedance, wherein the length of the first duration time of the electric pulse signal is 2 to 15 times of the length of the third duration time of the electric pulse signal, and the length of the fifth duration time of the electric pulse signal is 2 to 15 times of the length of the seventh duration time of the electric pulse signal.

In the method of using a multichannel stimulation system for regenerating damaged corneal nerves, at the step of confirming whether the reference impedance is exceeded, when the stimulation signal module applies a DC voltage of a predetermined amplitude to the 11-th channel and measures a current between the 11-th channel, the area where the 11-th channel is attached, the area where the 12-th channel is attached, and the 12-th channel, and the measured current is lower than a threshold value, or when the stimulation signal module applies a DC voltage of a predetermined amplitude to the 21-th channel and measures a current between the 21-th channel, the area where the 21-th channel is attached, the area where the 22-th channel is attached, and the 22-th channel, and the measured current is lower than the threshold value, it may be confirmed that the impedance exceeds the reference impedance, and when the current measured between the 11-th channel, the area where the 11-th channel is attached, the area where the 12-th channel is attached, and the 12-th channel is higher than the threshold value, the current measured between the 21-th channel, the area where the 21-th channel is attached, the area where the 22-th channel is attached, and the 22-th channel is higher than the threshold value, and any one of the current measured between the 11-th channel, the area where the 11-th channel is attached, the area where the 12-th channel is attached, and the 12-th channel and the current measured between the 21-th channel, the area where the 21-th channel is attached, the area where the 22-th channel 2122 is attached, and the 22-th channel 2122 is equal to or higher than 1.5 times of the other, it may be confirmed that the impedance exceeds the reference impedance.

In the method of using a multichannel stimulation system for regenerating damaged corneal nerves, at the step of confirming whether the reference impedance is exceeded, if it is confirmed that the impedance exceeds the reference impedance, the stimulation signal module may stop supply of the electric pulse signal of the adjusted magnitude of the absolute value.

In the method of using a multichannel stimulation system for regenerating damaged corneal nerves, at the step of confirming whether the reference impedance is exceeded, when the current measured between the 11-th channel, the area where the 11-th channel is attached, the area where the 12-th channel is attached, and the 12-th channel is higher than the threshold value, the current measured between the 21-th channel, the area where the 21-th channel is attached, the area where the 22-th channel is attached, and the 22-th channel is higher than the threshold value, and any one of the current measured between the 11-th channel, the area where the 11-th channel is attached, the area where the 12-th channel is attached, and the 12-th channel and the current measured between the 21-th channel, the area where the 21-th channel is attached, the area where the 22-th channel 2122 is attached, and the 22-th channel 2122 is lower than 1.5 times of the other, it may be confirmed that the impedance does not exceed the reference impedance, and the stimulation signal module may provide the 11-th channel, the 12-channel, the 21-th channel and the 22-th channel with an electric pulse signal of the adjusted magnitude of the absolute value.

In the method of using a multichannel stimulation system for regenerating damaged corneal nerves, magnitude of an absolute value of the positive current electric pulse signal of the first duration time of the electric pulse signal may be equal to magnitude of an absolute value of the negative current electric pulse signal of the third duration time of the electric pulse signal, and magnitude of an absolute value of the negative current electric pulse signal of the fifth duration time of the electric pulse signal may be equal to magnitude of an absolute value of the positive current electric pulse signal of the seventh duration time of the electric pulse signal.

In the method of using a multichannel stimulation system for regenerating damaged corneal nerves, magnitude of an absolute value of the positive current electric pulse signal of the first duration time of the electric pulse signal may be 2 to 15 times of magnitude of an absolute value of the negative current electric pulse signal of the third duration time of the electric pulse signal, and magnitude of an absolute value of the negative current electric pulse signal of the fifth duration time of the electric pulse signal may be 2 to 15 times of magnitude of an absolute value of the positive current electric pulse signal of the seventh duration time of the electric pulse signal.

In the method of using a multichannel stimulation system for regenerating damaged corneal nerves, the electric pulse signal may be in a charge-balanced state.

DETAILED DESCRIPTION OF THE PREFERRED EMBODIMENT

Figure 1:
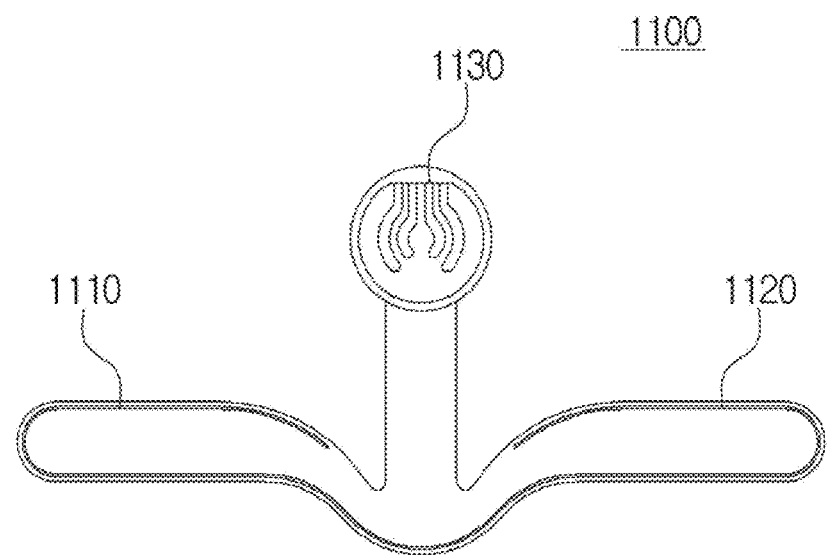
FIG. 1 is a view showing a multichannel unit employed in a method of using a multichannel stimulation system for regenerating damaged corneal nerves according to an embodiment of the present invention.

The detailed description of the present invention will be described below with reference to the accompanying drawings which show specific embodiments that the present invention can be embodied as an example. The embodiments are described in detail to be sufficient for those skilled in the art to embody the present invention. It should be understood that although the diverse embodiments of the present invention are different from each other, they do not need to be mutually exclusive. For example, specific shapes, structures and features described herein may be implemented as another embodiment without departing from the spirit and scope of the present invention in relation to an embodiment. In addition, it should be understood that the locations or arrangements of individual components in each disclosed embodiment may be changed without departing from the spirit and scope of the present invention.

Therefore, it is not intended to take the detailed description described below in a limited sense, and if appropriately explained, the scope of the present invention is limited only by the attached claims, together with all the scopes equivalent to the claims. Like reference numerals in the drawings denote like or similar functions throughout several aspects, and the length, area, thickness and the like and the shape may be exaggerated for convenience.

Hereinafter, a system employed in a method of using a multichannel stimulation system for regenerating damaged corneal nerves according to an embodiment of the present invention will be described with reference to FIGS. 1 to 6.

Figure 2:
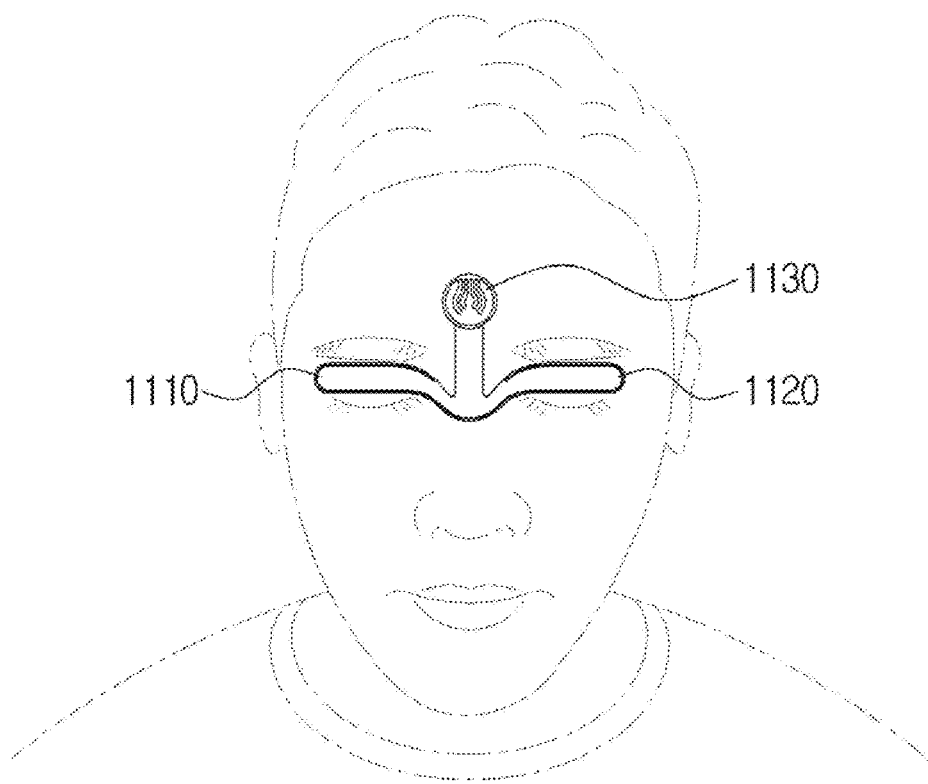
FIG. 2 is a view showing a state of attaching a multichannel unit employed in a method of using a multichannel stimulation system for regenerating damaged corneal nerves according to an embodiment of the present invention in an area close to the eyes of a person.
Figure 3:
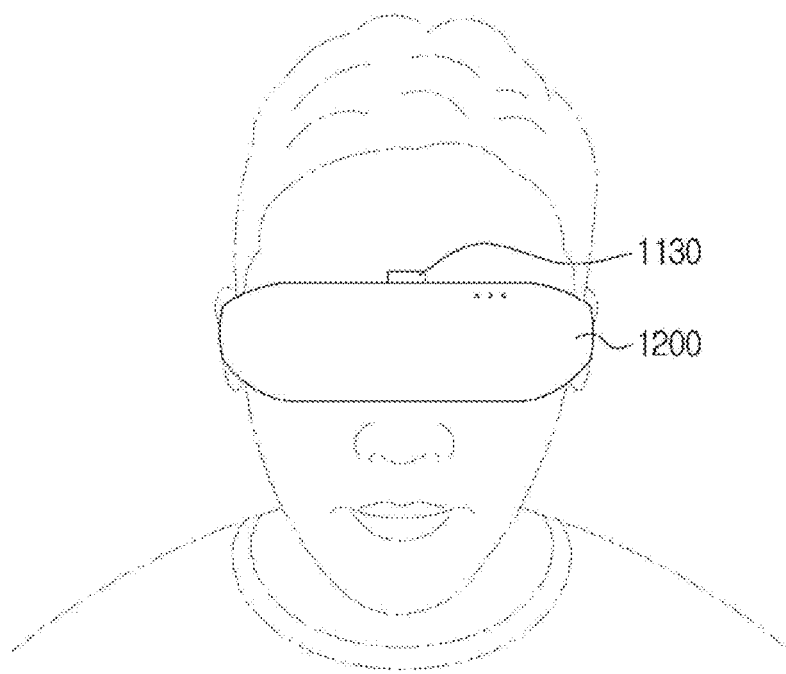
FIG. 3 is a view showing a state of attaching a multichannel unit and a stimulation signal module employed in a method of using a multichannel stimulation system for regenerating damaged corneal nerves according to an embodiment of the present invention in an area close to the eyes of a person.
Figure 4:
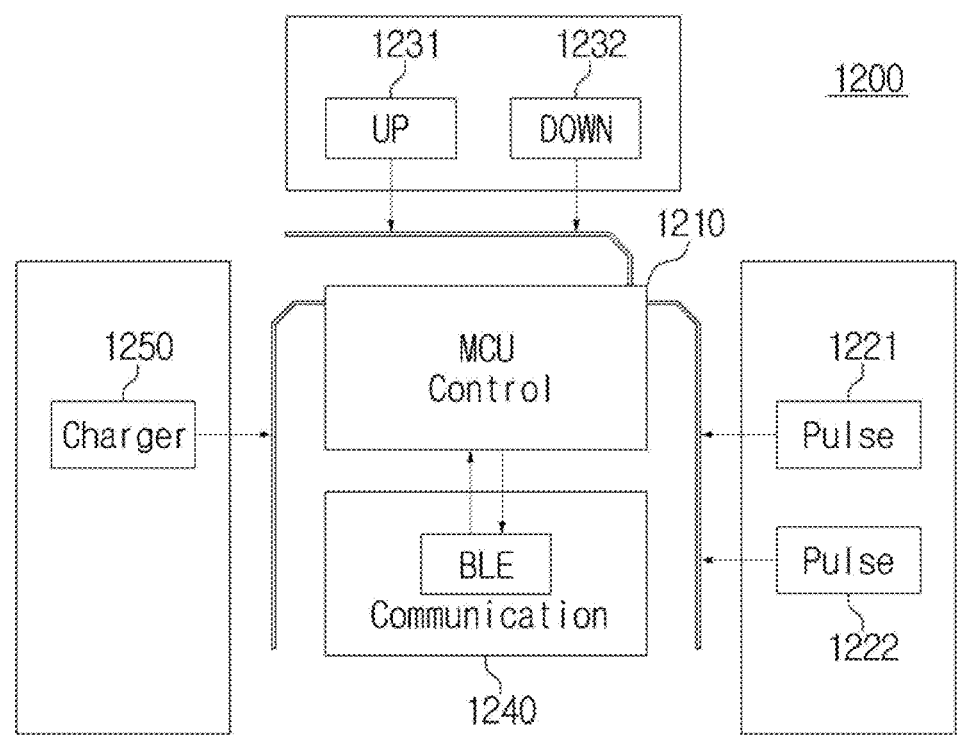
FIG. 4 is a block diagram showing a stimulation signal module employed in a method of using a multichannel stimulation system for regenerating damaged corneal nerves according to an embodiment of the present invention.
Figure 5:
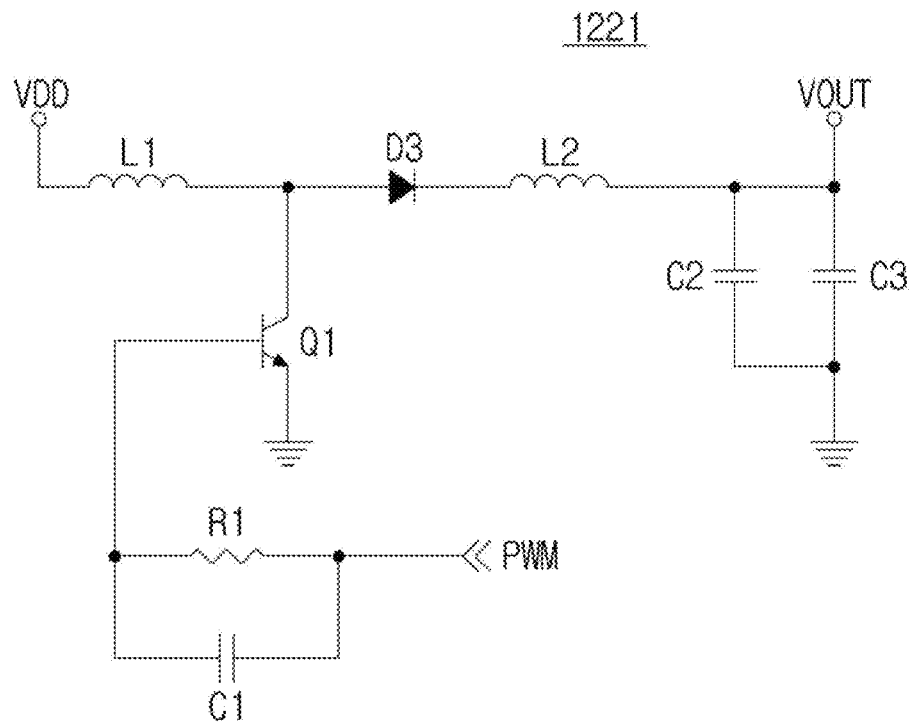
FIG. 5 is a voltage control circuit diagram according to pressure recovery of an up button or a down button arranged in a stimulation signal module employed in a method of using a multichannel stimulation system for regenerating damaged corneal nerves according to an embodiment of the present invention.
Figure 6:
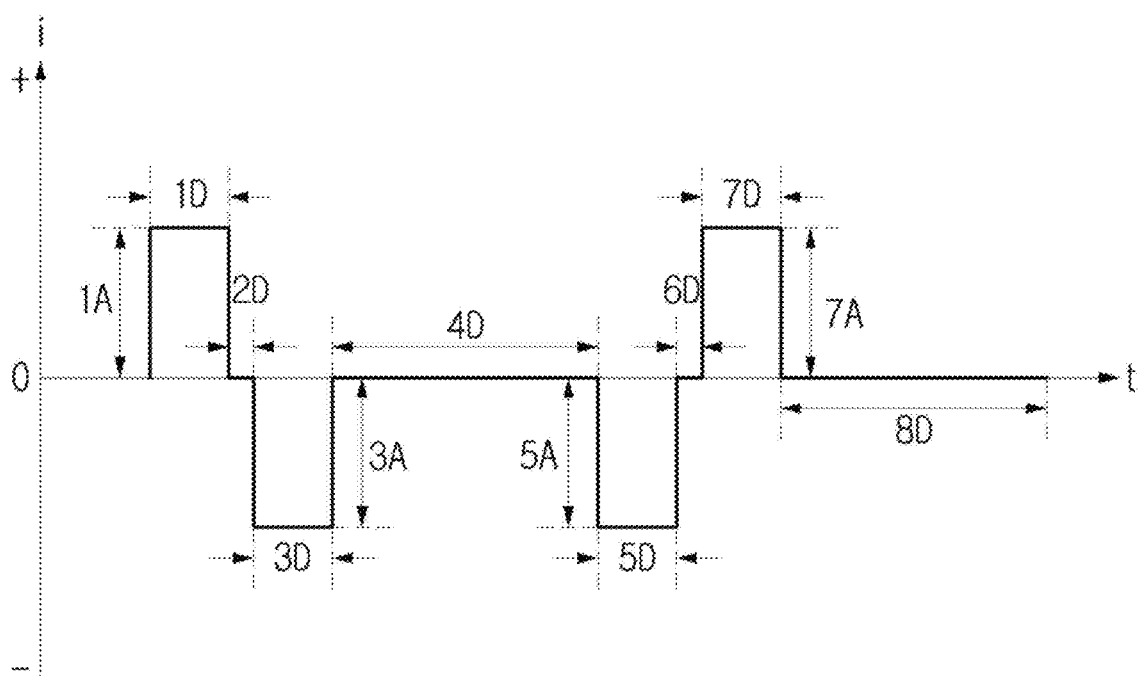
FIG. 6 is a view showing an electric pulse signal provided by a stimulation signal module employed in a method of using a multichannel stimulation system for regenerating damaged corneal nerves according to an embodiment of the present invention.

FIG. 1 is a view showing a multichannel unit employed in a method of using a multichannel stimulation system for regenerating damaged corneal nerves according to an embodiment of the present invention, FIG. 2 is a view showing a state of attaching a multichannel unit employed in a method of using a multichannel stimulation system for regenerating damaged corneal nerves according to an embodiment of the present invention in an area close to the eyes of a person, FIG. 3 is a view showing a state of attaching a multichannel unit and a stimulation signal module employed in a method of using a multichannel stimulation system for regenerating damaged corneal nerves according to an embodiment of the present invention in an area close to the eyes of a person, FIG. 4 is a block diagram showing a stimulation signal module employed in a method of using a multichannel stimulation system for regenerating damaged corneal nerves according to an embodiment of the present invention, FIG. 5 is a voltage control circuit diagram according to pressure recovery of an up button or a down button arranged in a stimulation signal module employed in a method of using a multichannel stimulation system for regenerating damaged corneal nerves according to an embodiment of the present invention, and FIG. 6 is a view showing an electric pulse signal provided by a stimulation signal module employed in a method of using a multichannel stimulation system for regenerating damaged corneal nerves according to an embodiment of the present invention.

As shown in FIGS. 1 and 2, a multichannel unit 1100 employed in a method of using a multichannel stimulation system for regenerating damaged corneal nerves according to an embodiment of the present invention includes a first channel 1110 formed of a conductive material and attached between an area above the left eye and the left eyebrow to transfer a stimulation signal, a second channel 1120 formed of a conductive material and attached between an area above the right eye and the right eyebrow to transfer the stimulation signal, and a contactor 1130 formed between the first channel 1110 and the second channel 1120 in one piece together with the first channel 1110 and the second channel 1120 to electrically contact with a stimulation signal module 1200. Here, the first channel 1110, the second channel 1120 and the contactor 1130 may be formed of Ag, AgCl, Au, Pt or stainless steel.

In addition, the stimulation signal module 1200 provides the first channel 1110 and the second channel 1120 with an electric pulse signal as the stimulation signal and may be worn between the eyes and the nose of a person like wearing goggles as shown in FIG. 3, and a magnet is arranged in each of the contactor 1130 of the multichannel unit 1100 and the stimulation signal module 1200, and when the contactor 1130 of the multichannel unit 1100 and the stimulation signal module 1200 approach each other within a predetermined range, the contactor 1130 of the multichannel unit 1100 and the stimulation signal module 1200 are self-aligned by the attraction force of the magnets.

Meanwhile, as shown in FIG. 4, the stimulation signal module 1200 described above includes stimulation signal providing units 1221 and 1222 for generating an electric pulse signal, a control unit 1210 for controlling the stimulation signal providing units 1221 and 1222, an up button 1231, a down button 1232, a communication unit 1240 communicating with the outside, and a charge unit 1250.

When a pressure is applied to the up button 1231 of the stimulation signal module 1200, the magnitude of the electric pulse signal is increased in proportion to the number of times of applying the pressure to the up button 1231, and when a pressure is applied to the down button 1232 of the stimulation signal module 1200, the magnitude of the electric pulse signal is decreased in inverse proportion to the number of times of applying the pressure to the down button 1232.

Specifically, when a pressure is applied to the up button 1231, the stimulation signal module 1200 controls to increase the magnitude of the electric pulse signal by adjusting the number of pulses of a pulse width modulation (PWM) signal in proportion to the number of times of applying the pressure to the up button 1231, and when a pressure is applied to the down button 1232, the stimulation signal module 1200 controls to decrease the magnitude of the electric pulse signal by adjusting the number of pulses of the pulse width modulation (PWM) signal in inverse proportion to the number of times of applying the pressure to the down button 1232.

For example, when the number of times of applying pressure to the up button 1231 is three, as shown in FIG. 5, three pulse width modulation (PWM) signals are transferred to the transistor Q1, and the transistor Q1 is turned on during the three pulse width modulation (PWM) signals, and therefore, the voltage boosted by the inductor L1 is charged in the capacitors C2 and C3 in proportion to the change of current which flows during the three pulse width modulation (PWM) signals. Accordingly, since the boosted voltage is charged in the capacitors C2 and C3 in proportion to the number of pulse width modulation (PWM) signals, it may be controlled to increase the magnitude of the electric pulse signal in proportion to the number of times of applying the pressure to the up button 1231 and to decrease the magnitude of the electric pulse signal in inverse proportion to the number of times of applying the pressure to the down button 1232.

As shown in FIG. 6, the electric pulse signal is configured of a positive current pulse signal during a first duration time 1D, a zero current electric pulse signal during a second duration time 2D following the first duration time 1D, a negative current pulse signal during a third duration time 3D following the second duration time 2D, a zero current electric pulse signal during a fourth duration time 4D following the third duration time 3D, a negative current pulse signal during a fifth duration time 5D following the fourth duration time 4D, a zero current electric pulse signal during a sixth duration time 6D following the fifth duration time 5D, a positive current pulse signal during a seventh duration time 7D following the sixth duration time 6D, and a zero current electric pulse signal during an eighth duration time 8D following the seventh duration time 7D.

The fourth duration time 4D of the electric pulse signal is 5 to 2,000 times of the second duration time 2D of the electric pulse signal, and the eighth duration time 8D of the electric pulse signal is 5 to 2,000 times of the sixth duration time 6D of the electric pulse signal.

For example, when the second duration time 2D of the electric pulse signal is 5 μs, the fourth duration time 4D of the electric pulse signal is 25 to 10,000 μs, and when the sixth duration time 6D of the electric pulse signal is 5 μs, the eighth duration time 8D of the electric pulse signal is 25 to 10,000 μs.

In addition, magnitude 1A of the absolute value of the positive current electric pulse signal of the first duration time 1D of the electric pulse signal is equal to magnitude 3A of the absolute value of the negative current electric pulse signal of the third duration time 3D of the electric pulse signal, and magnitude 5A of the absolute value of the negative current electric pulse signal of the fifth duration time 5D of the electric pulse signal is equal to magnitude 7A of the absolute value of the positive current electric pulse signal of the seventh duration time 7D of the electric pulse signal.

Meanwhile, magnitude 1A of the absolute value of the positive current electric pulse signal of the first duration time 1D of the electric pulse signal is 2 to 15 times of magnitude 3A of the absolute value of the negative current electric pulse signal of the third duration time 3D of the electric pulse signal, and magnitude 5A of the absolute value of the negative current electric pulse signal of the fifth duration time 5D of the electric pulse signal is 2 to 15 times of magnitude 7A of the absolute value of the positive current electric pulse signal of the seventh duration time 7D of the electric pulse signal.

For example, the electric pulse signal is configured to be in a charge-balanced state by configuring the absolute value of the positive current electric pulse signal of the first duration time 1D to be 2 to 15 mA when the absolute value of the negative current electric pulse signal of the third duration time 3D is 1 mA during the equal first duration time 1D and third duration time 3D, and the absolute value of the negative current electric pulse signal of the fifth duration time 5D to be 2 to 15 mA when the absolute value of the positive current electric pulse signal of the seventh duration time 7D is 1 mA during the equal fifth duration time 5D and seventh duration time 7D.

In addition, the length of the first duration time 1D of the electric pulse signal is equal to the length of the third duration time 3D of the electric pulse signal, and the length of the fifth duration time 5D of the electric pulse signal is equal to the length of the seventh duration time 7D of the electric pulse signal.

Meanwhile, the length of the first duration time 1D of the electric pulse signal is 2 to 15 times of the length of the third duration time 3D of the electric pulse signal, and the length of the fifth duration time 5D of the electric pulse signal is 2 to 15 times of the length of the seventh duration time 7D of the electric pulse signal.

For example, the electric pulse signal is configured to be in a charge-balanced state by configuring the first duration time 1D to be 20 to 300 μs when magnitude 1A of the absolute value of the positive current electric pulse signal of the first duration time 1D is equal to magnitude 3A of the absolute value of the negative current electric pulse signal of the third duration time 3D and the length of the third duration time 3D is 10 μs, and the fifth duration time 5D to be 20 to 300 μs when magnitude 5A of the absolute value of the negative current electric pulse signal of the fifth duration time 5D is equal to magnitude 7A of the absolute value of the positive current electric pulse signal of the seventh duration time 7D and the length of the seventh duration time 7D is 10 μs.

Meanwhile, the stimulation signal module 1200 provides the first channel 1110 with the electric pulse signal of the first duration time 1D and the electric pulse signal of the seventh duration time 7D, and provides the second channel 1120 with the electric pulse signal of the third duration time 3D and the electric pulse signal of the fifth duration time 5D.

Hereinafter, a method of using a multichannel stimulation system for regenerating damaged corneal nerves according to an embodiment of the present invention will be described.

First, as shown in FIG. 3, the contactor 1130 of the multichannel unit 1100 electrically contacts with the stimulation signal module 1200 while the first channel 1110 is attached between an area above the left eye and the left eyebrow, the second channel 1120 is attached between an area above the right eye and the right eyebrow, and the stimulation signal module 1200 is worn between the eyes and the nose.

Next, the stimulation signal module 1200 supplies an electric pulse signal configured of a positive current pulse signal during a first duration time 1D, a zero current electric pulse signal during a second duration time 2D following the first duration time 1D, a negative current pulse signal during a third duration time 3D following the second duration time 2D, a zero current electric pulse signal during a fourth duration time 4D following the third duration time 3D, a negative current pulse signal during a fifth duration time 5D following the fourth duration time 4D, a zero current electric pulse signal during a sixth duration time 6D following the fifth duration time 5D, a positive current pulse signal during a seventh duration time 7D following the sixth duration time 6D, and a zero current electric pulse signal during an eighth duration time 8D following the seventh duration time 7D.

Next, the stimulation signal module 1200 transfers the electric pulse signal of the first duration time 1D and the electric pulse signal of the seventh duration time 7D to the first channel 1110, and the electric pulse signal of the third duration time 3D and the electric pulse signal of the fifth duration time 5D to the second channel 1120.

Next, as it is controlled to increase the magnitude of the absolute value of the electric pulse signal in proportion to the number of times of applying the pressure to the up button 1231 of the stimulation signal module 1200 and to decrease the magnitude of the absolute value of the electric pulse signal in inverse proportion to the number of times of applying the pressure to the down button 1232 of the stimulation signal module 1200, when the magnitude of the absolute value of the electric pulse signal desired by a user is adjusted, the adjusted magnitude of the absolute value of the electric pulse signal is maintained.

Next, impedance between the first channel 1110 and an area where the first channel 1110 is attached and impedance between the second channel 1120 and an area where the second channel 1120 is attached are measured, and it is confirmed whether the impedance measured between the first channel 1110 and the area where the first channel 1110 is attached and the impedance measured between the second channel 1120 and the area where the second channel 1120 is attached exceed a reference impedance.

Here, the impedance between the first channel 1110 and the area where the first channel 1110 is attached and the impedance between the second channel 1120 and the area where the second channel 1120 is attached are measured whenever one electric pulse signal is transmitted, and an average of about ten measured values may be used.

Specifically, the stimulation signal module 1200 applies a DC voltage of a predetermined amplitude to the first channel 1110, measures a current between the first channel 1110, the area where the first channel 1110 is attached, the area where the second channel 1120 is attached, and the second channel 1120, and confirms that the impedance exceeds the reference impedance when the measured current is lower than a threshold value.

Here, when the measured current is lower than a threshold value, it may be assumed that an attachment defect is generated in the first channel 1110 or an attachment defect is generated in the second channel 1120, and thereafter, the stimulation signal module 1200 stops supply of the electric pulse signal of the adjusted magnitude of the absolute value.

Meanwhile, if it is confirmed that the current measured between the first channel 1110, the area where the first channel 1110 is attached, the area where the second channel 1120 is attached, and the second channel 1120 is higher than the threshold value and thus the impedance does not exceed the reference impedance, the stimulation signal module 1200 provides the first channel 1110 and the second channel 1120 with an electric pulse signal of the adjusted magnitude of the absolute value.

Hereinafter, a system employed in a method of using a multichannel stimulation system for regenerating damaged corneal nerves according to another embodiment of the present invention will be described with reference to FIGS. 7 to 12.

Figure 7:
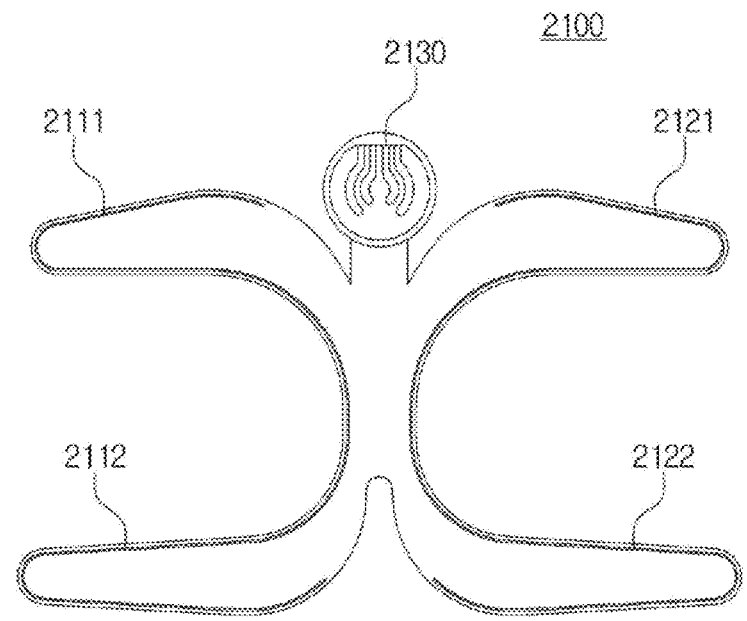
FIG. 7 is a view showing a multichannel unit employed in a method of using a multichannel stimulation system for regenerating damaged corneal nerves according to another embodiment of the present invention.
Figure 8:
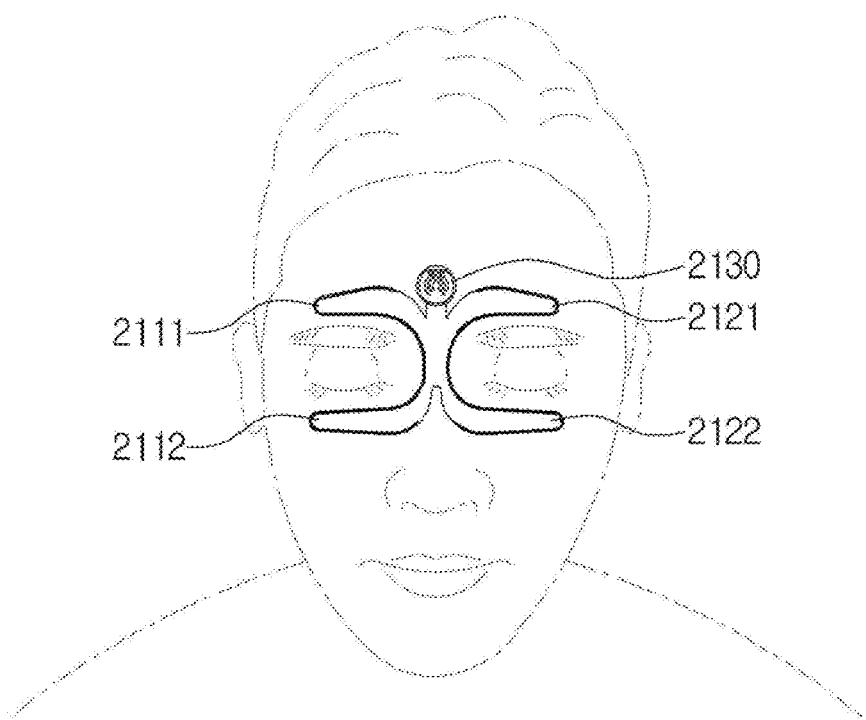
FIG. 8 is a view showing a state of attaching a multichannel unit employed in a method of using a multichannel stimulation system for regenerating damaged corneal nerves according to an embodiment of the present invention in an area close to the eyes of a person.
Figure 9:
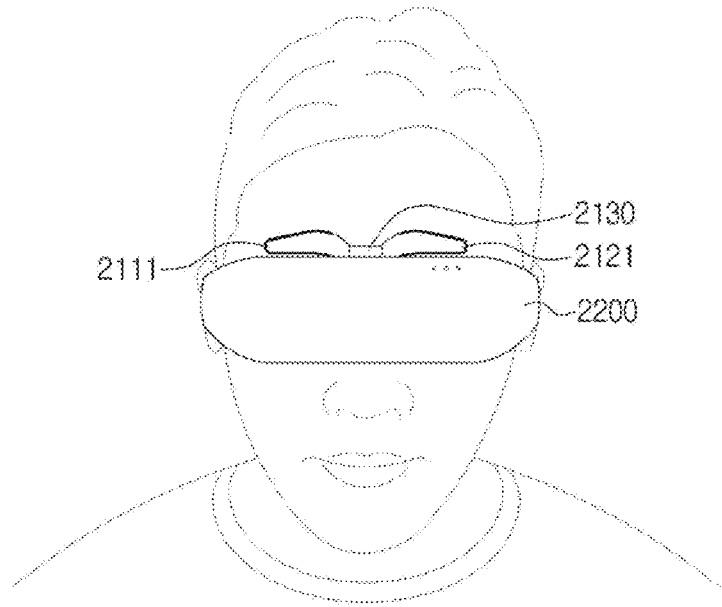
FIG. 9 is a view showing a state of attaching a multichannel unit and a stimulation signal module employed in a method of using a multichannel stimulation system for regenerating damaged corneal nerves according to an embodiment of the present invention in an area close to the eyes of a person.
Figure 10:
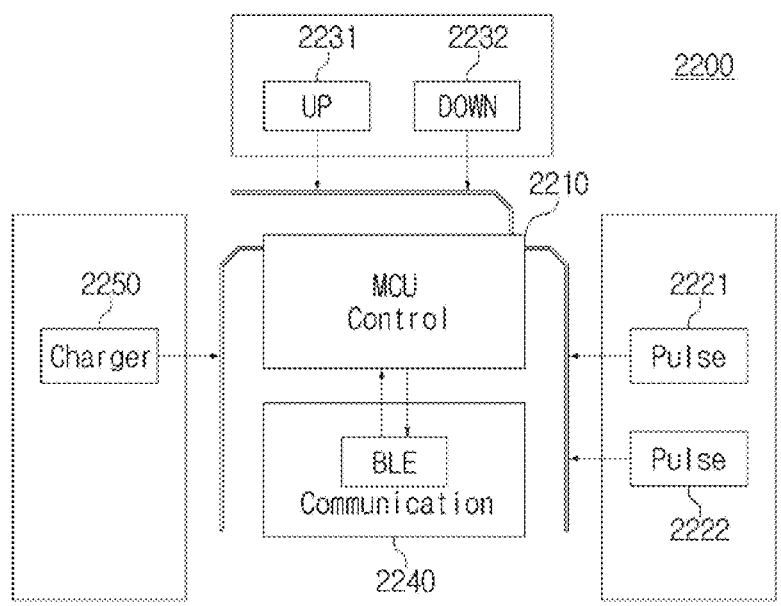
FIG. 10 is a block diagram showing a stimulation signal module employed in a method of using a multichannel stimulation system for regenerating damaged corneal nerves according to an embodiment of the present invention.
Figure 11:
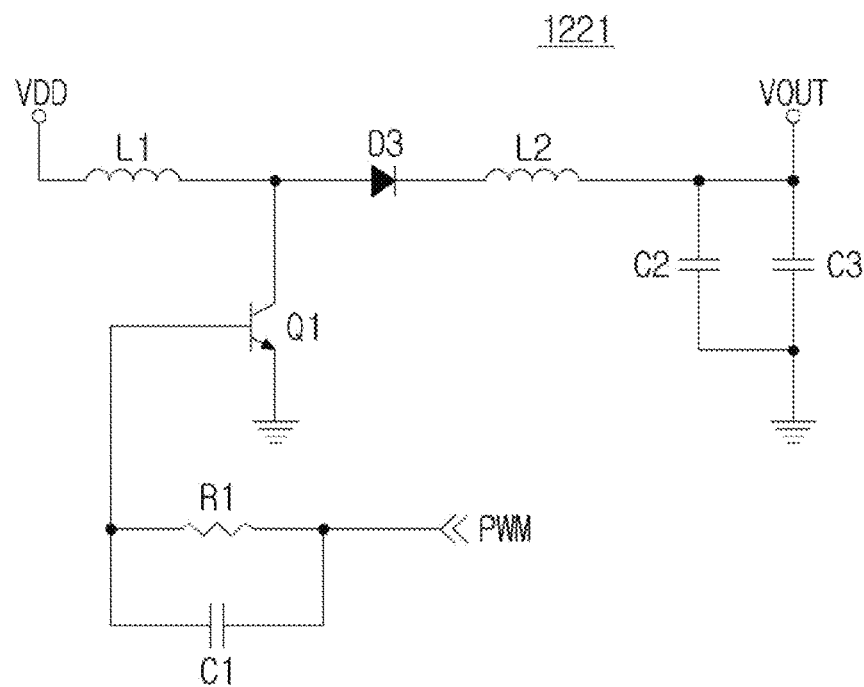
FIG. 11 is a voltage control circuit diagram according to pressure recovery of an up button or a down button employed in a stimulation signal module employed in a method of using a multichannel stimulation system for regenerating damaged corneal nerves according to an embodiment of the present invention.
Figure 12:
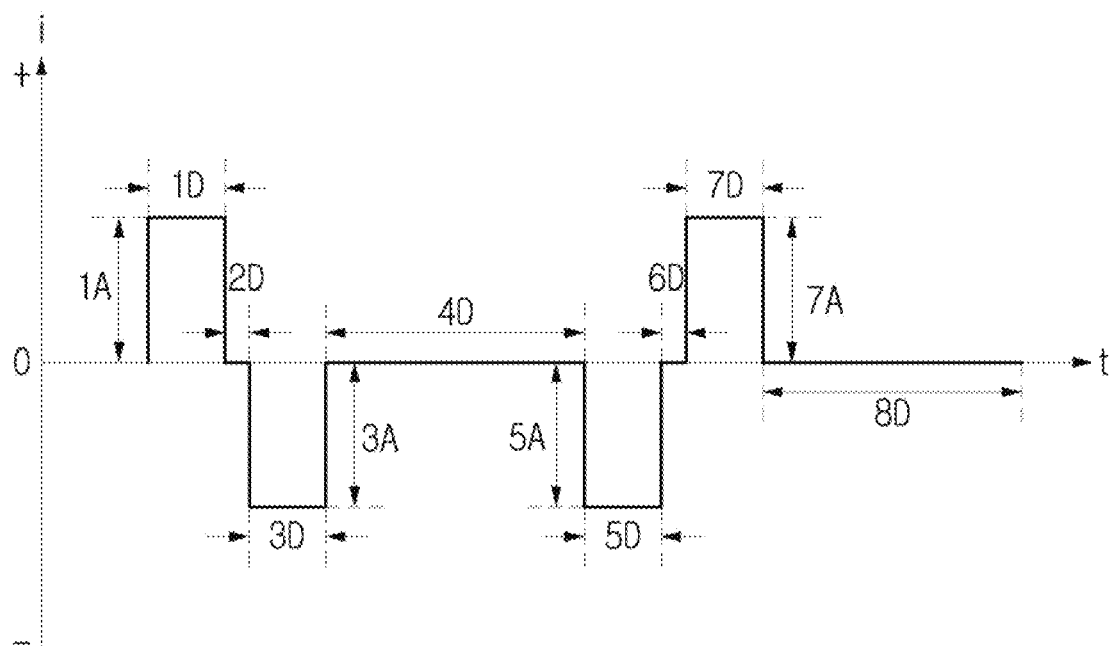
FIG. 12 is a view showing an electric pulse signal provided by a stimulation signal module employed in a method of using a multichannel stimulation system for regenerating damaged corneal nerves according to an embodiment of the present invention.

FIG. 7 is a view showing a multichannel unit employed in a method of using a multichannel stimulation system for regenerating damaged corneal nerves according to another embodiment of the present invention, FIG. 8 is a view showing a state of attaching a multichannel unit employed in a method of using a multichannel stimulation system for regenerating damaged corneal nerves according to an embodiment of the present invention in an area close to the eyes of a person, FIG. 9 is a view showing a state of attaching a multichannel unit and a stimulation signal module employed in a method of using a multichannel stimulation system for regenerating damaged corneal nerves according to an embodiment of the present invention in an area close to the eyes of a person, FIG. 10 is a block diagram showing a stimulation signal module employed in a method of using a multichannel stimulation system for regenerating damaged corneal nerves according to an embodiment of the present invention, FIG. 11 is a voltage control circuit diagram according to pressure recovery of an up button or a down button employed in a stimulation signal module employed in a method of using a multichannel stimulation system for regenerating damaged corneal nerves according to an embodiment of the present invention, and FIG. 12 is a view showing an electric pulse signal provided by a stimulation signal module employed in a method of using a multichannel stimulation system for regenerating damaged corneal nerves according to an embodiment of the present invention.

As shown in FIGS. 7 and 8, a multichannel unit 2100 employed in a method of using a multichannel stimulation system for regenerating damaged corneal nerves according to another embodiment of the present invention includes a 11-th channel 2111 formed of a conductive material and attached above the left eyebrow to transfer a stimulation signal, a 12-th channel 2112 formed of a conductive material and attached below the left eye to transfer the stimulation signal, a 21-th channel 2121 formed of a conductive material and attached above the right eyebrow to transfer the stimulation signal, a 22-th channel 2122 formed of a conductive material and attached below the right eye to transfer the stimulation signal, and a contactor 2130 formed between the 11-th channel 2111 and the 21-th channel 2121 in one piece together with the 11-th channel 2111, the 12-th channel 2112, the 21-th channel 2121, and the 22-th channel 2122 to electrically contact with the stimulation signal module. Here, the 11-th channel 2111, the 12-th channel 2112, the 21-th channel 2121, the 22-th channel 2122 and the contactor 2130 may be formed of Ag, AgCl, Au, Pt or stainless steel.

In addition, the stimulation signal module 2200 provides the 11-th channel 2111, the 12-th channel 2112, the 21-th channel 2121, and the 22-th channel 2122 with an electric pulse signal as the stimulation signal and may be worn between the eyes and the nose of a person like wearing goggles as shown in FIG. 9, and a magnet is arranged in each of the contactor 2130 of the multichannel unit 2100 and the stimulation signal module 2200, and when the contactor 2130 of the multichannel unit 2100 and the stimulation signal module 2200 approach each other within a predetermined range, the contactor 2130 of the multichannel unit 2100 and the stimulation signal module 2200 are self-aligned by the attraction force of the magnets.

Meanwhile, as shown in FIG. 10, the stimulation signal module 2200 described above includes stimulation signal providing units 2221 and 2222 for generating a electric pulse signal, a control unit 2210 for controlling the stimulation signal providing units 2221 and 2222, an up button 2231, a down button 2232, a communication unit 2240 communicating with the outside, and a charge unit 2250.

When a pressure is applied to the up button 2231 of the stimulation signal module 2200, the magnitude of the electric pulse signal is increased in proportion to the number of times of applying the pressure to the up button 2231, and when a pressure is applied to the down button 2232 of the stimulation signal module 2200, the magnitude of the electric pulse signal is decreased in inverse proportion to the number of times of applying the pressure to the down button 2232.

Specifically, when a pressure is applied to the up button 2231, the stimulation signal module 2200 controls to increase the magnitude of the electric pulse signal by adjusting the number of pulses of a pulse width modulation (PWM) signal in proportion to the number of times of applying the pressure to the up button 2231, and when a pressure is applied to the down button 2232, the stimulation signal module 2200 controls to decrease the magnitude of the electric pulse signal by adjusting the number of pulses of the pulse width modulation (PWM) signal in inverse proportion to the number of times of applying the pressure to the down button 2232.

For example, when the number of times of applying pressure to the up button 2231 is three, as shown in FIG. 11, three pulse width modulation (PWM) signals are transferred to the transistor Q1, and the transistor Q1 is turned on during the three pulse width modulation (PWM) signals, and therefore, the voltage boosted by the inductor L1 is charged in the capacitors C2 and C3 in proportion to the change of current which flows during the three pulse width modulation (PWM) signals. Accordingly, since the boosted voltage is charged in the capacitors C2 and C3 in proportion to the number of pulse width modulation (PWM) signals, it may be controlled to increase the magnitude of the electric pulse signal in proportion to the number of times of applying the pressure to the up button 2231 and to decrease the magnitude of the electric pulse signal in inverse proportion to the number of times of applying the pressure to the down button 2232.

As shown in FIG. 12, the electric pulse signal is configured of a positive current pulse signal during a first duration time 1D, a zero current electric pulse signal during a second duration time 2D following the first duration time 1D, a negative current pulse signal during a third duration time 3D following the second duration time 2D, a zero current electric pulse signal during a fourth duration time 4D following the third duration time 3D, a negative current pulse signal during a fifth duration time 5D following the fourth duration time 4D, a zero current electric pulse signal during a sixth duration time 6D following the fifth duration time 5D, a positive current pulse signal during a seventh duration time 7D following the sixth duration time 6D, and a zero current electric pulse signal during an eighth duration time 8D following the seventh duration time 7D.

The fourth duration time 4D of the electric pulse signal is 5 to 2,000 times of the second duration time 2D of the electric pulse signal, and the eighth duration time 8D of the electric pulse signal is 5 to 2,000 times of the sixth duration time 6D of the electric pulse signal.

For example, when the second duration time 2D of the electric pulse signal is 5 µs, the fourth duration time 4D of the electric pulse signal is 25 to 10,000 µs, and when the sixth duration time 6D of the electric pulse signal is 5 µs, the eighth duration time 8D of the electric pulse signal is 25 to 10,000 µs.

In addition, magnitude 1A of the absolute value of the positive current electric pulse signal of the first duration time 1D of the electric pulse signal is equal to magnitude 3A of the absolute value of the negative current electric pulse signal of the third duration time 3D of the electric pulse signal, and magnitude 5A of the absolute value of the negative current electric pulse signal of the fifth duration time 5D of the electric pulse signal is equal to magnitude 7A of the absolute value of the positive current electric pulse signal of the seventh duration time 7D of the electric pulse signal.

Meanwhile, magnitude 1A of the absolute value of the positive current electric pulse signal of the first duration time 1D of the electric pulse signal is 2 to 15 times of magnitude 3A of the absolute value of the negative current electric pulse signal of the third duration time 3D of the electric pulse signal, and magnitude 5A of the absolute value of the negative current electric pulse signal of the fifth duration time 5D of the electric pulse signal is 2 to 15 times of magnitude 7A of the absolute value of the positive current electric pulse signal of the seventh duration time 7D of the electric pulse signal.

For example, the electric pulse signal is configured to be in a charge-balanced state by configuring the absolute value of the positive current electric pulse signal of the first duration time 1D to be 2 to 15 mA when the absolute value of the negative current electric pulse signal of the third duration time 3D is 1 mA during the equal first duration time 1D and third duration time 3D, and the absolute value of the negative current electric pulse signal of the fifth duration time 5D to be 2 to 15 mA when the absolute value of the positive current electric pulse signal of the seventh duration time 7D is 1 mA during the equal fifth duration time 5D and seventh duration time 7D.

In addition, the length of the first duration time 1D of the electric pulse signal is equal to the length of the third duration time 3D of the electric pulse signal, and the length of the fifth duration time 5D of the electric pulse signal is equal to the length of the seventh duration time 7D of the electric pulse signal.

Meanwhile, the length of the first duration time 1D of the electric pulse signal is 2 to 15 times of the length of the third duration time 3D of the electric pulse signal, and the length of the fifth duration time 5D of the electric pulse signal is 2 to 15 times of the length of the seventh duration time 7D of the electric pulse signal.

For example, the electric pulse signal is configured to be in a charge-balanced state by configuring the first duration time 1D to be 20 to 300 µs when magnitude 1A of the absolute value of the positive current electric pulse signal of the first duration time 1D is equal to magnitude 3A of the absolute value of the negative current electric pulse signal of the third duration time 3D and the length of the third duration time 3D is 10 µs, and the fifth duration time 5D to be 20 to 300 µs when magnitude 5A of the absolute value of the negative current electric pulse signal of the fifth duration time 5D is equal to magnitude 7A of the absolute value of the positive current electric pulse signal of the seventh duration time 7D and the length of the seventh duration time 7D is 10 µs.

Meanwhile, the stimulation signal module 2200 provides the 11-th channel 2111 with the electric pulse signal of the first duration time 1D and the electric pulse signal of the seventh duration time 7D, provides the 12-th channel 2112 with the electric pulse signal of the third duration time 3D and the electric pulse signal of the fifth duration time 5D, provides the 21-th channel 2121 with the electric pulse signal of the first duration time 1D and the electric pulse signal of the seventh duration time 7D, and provides the 22-th channel 2122 with the electric pulse signal of the third duration time 3D and the electric pulse signal of the fifth duration time 5D. That is, the stimulation signal module 2200 provides the same electric pulse signal to the 11-th channel 2111 and the 21-th channel 2121, and provides the same electric pulse signal to the 12-th channel 2112 and the 22-th channel 2122.

Hereinafter, a method of using a multichannel stimulation system for regenerating damaged corneal nerves according to another embodiment of the present invention will be described.

First, as shown in FIG. 9, while the 11-th channel 2111 is attached above the left eyebrow, the 12-th channel 2112 is attached below the left eye, the 21-th channel 2121 is attached above the right eyebrow, the 22-th channel 2122 is attached below the right eye, and the stimulation signal module 2200 is worn between the eyes and the nose, the contactor 2130 of the multichannel unit 2100 electrically contacts with the stimulation signal module 2200.

Next, the stimulation signal module 2200 supplies an electric pulse signal configured of a positive current pulse signal during a first duration time 1D, a zero current electric pulse signal during a second duration time 2D following the first duration time 1D, a negative current pulse signal during a third duration time 3D following the second duration time 2D, a zero current electric pulse signal during a fourth duration time 4D following the third duration time 3D, a negative current pulse signal during a fifth duration time 5D following the fourth duration time 4D, a zero current electric pulse signal during a sixth duration time 6D following the fifth duration time 5D, a positive current pulse signal during a seventh duration time 7D following the sixth duration time 6D, and a zero current electric pulse signal during an eighth duration time 8D following the seventh duration time 7D.

Next, the stimulation signal module 2200 transfers the electric pulse signal of the first duration time 1D and the electric pulse signal of the seventh duration time 7D to the 11-th channel 2111, transfers the electric pulse signal of the third duration time 3D and the electric pulse signal of the fifth duration time 5D to the 12-th channel 2112, transfers the electric pulse signal of the first duration time 1D and the electric pulse signal of the seventh duration time 7D to the 21-th channel 2121, and transfers the electric pulse signal of the third duration time 3D and the electric pulse signal of the fifth duration time 5D to the 22-th channel 2122.

Next, as it is controlled to increase the magnitude of the absolute value of the electric pulse signal in proportion to the number of times of applying the pressure to the up button 2231 of the stimulation signal module 2200 and to decrease the magnitude of the absolute value of the electric pulse signal in inverse proportion to the number of times of applying the pressure to the down button 2232 of the stimulation signal module 2200, when the magnitude of the absolute value of the electric pulse signal desired by a user is adjusted, the adjusted magnitude of the absolute value of the electric pulse signal is maintained.

Next, impedance between the 11-th channel 2111 and an area where the 11-th channel 2111 is attached and impedance between the 12-th channel 2112 and an area where the 12-th channel 2112 is attached are measured, and impedance between the 21-th channel 2121 and an area where the 21-th channel 2121 is attached and impedance between the 22-th channel 2122 and an area where the 22-th channel 2122 is attached are measured, and then it is confirmed whether the impedance between the 11-th channel 2111 and the area where the 11-th channel 2111 is attached and the impedance between the 12-th channel 2112 and the area where the 12-th channel 2112 is attached exceed a reference impedance, and whether the impedance between the 21-th channel 2121 and the area where the 21-th channel 2121 is attached and the impedance between the 22-th channel 2122 and the area where the 22-th channel 2122 is attached exceed a reference impedance.

Here, the impedance between the 11-th channel 2111 and the area where the 11-th channel 2111 is attached, the impedance between the 12-th channel 2112 and the area where the 12-th channel 2112 is attached, the impedance between the 21-th channel 2121 and the area where the 21-th channel 2121 is attached, and the impedance between the 22-th channel 2122 and the area where the 22-th channel 2122 is attached are measured whenever one electric pulse signal is transmitted, and an average of about ten measured values may be used.

Specifically, the stimulation signal module 2200 confirms that the impedance exceeds the reference impedance when the stimulation signal module 2200 applies a DC voltage of a predetermined amplitude to the 11-th channel 2111 and measures a current between the 11-th channel 2111, the area where the 11-th channel 2111 is attached, the area where the 12-th channel 2112 is attached, and the 12-th channel 2112, and the measured current is lower than a threshold value, or when the stimulation signal module 2200 applies a DC voltage of a predetermined amplitude to the 21-th channel 2121 and measures a current between the 21-th channel 2121, the area where the 21-th channel 2121 is attached, the area where the 22-th channel 2122 is attached, and the 22-th channel 2122, and the measured current is lower than a threshold value, and the stimulation signal module 2200 confirms that the impedance exceeds the reference impedance when the current measured between the 11-th channel 2111, the area where the 11-th channel 2111 is attached, the area where the 12-th channel 2112 is attached, and the 12-th channel 2112 is higher than the threshold value, the current measured between the 21-th channel 2121, the area where the 21-th channel 2121 is attached, the area where the 22-th channel 2122 is attached, and the 22-th channel 2122 is higher than the threshold value, and any one of the current measured between the 11-th channel 2111, the area where the 11-th channel 2111 is attached, the area where the 12-th channel 2112 is attached, and the 12-th channel 2112 and the current measured between the 21-th channel 2121, the area where the 21-th channel 2121 is attached, the area where the 22-th channel 2122 is attached, and the 22-th channel 2122 is equal to or higher than 1.5 times of the other.

For example, it is confirmed that the impedance exceeds the reference impedance when the threshold current is 0.1 mA and the current measured between the 11-th channel 2111, the area where the 11-th channel 2111 is attached, the area where the 12-th channel 2112 is attached, and the 12-th channel 2112 is lower than 0.01 mA, when the threshold current is 0.1 mA and the current measured between the 21-th channel 2121, the area where the 21-th channel 2121 is attached, the area where the 22-th channel 2122 is attached, and the 22-th channel 2122 is lower than 0.01 mA, when the threshold current is 0.1 mA, the current measured between the 11-th channel 2111, the area where the 11-th channel 2111 is attached, the area where the 12-th channel 2112 is attached, and the 12-th channel 2112 is 0.03 mA, and the current measured between the 21-th channel 2121, the area where the 21-th channel 2121 is attached, the area where the 22-th channel 2122 is attached, and the 22-th channel 2122 is 0.01 to 0.03 mA, or 0.45 mA or higher, or when the threshold current is 0.1 mA, the current measured between the 21-th channel 2121, the area where the 21-th channel 2121 is attached, the area where the 22-th channel 2122 is attached, and the 22-th channel 2122 is 0.03 mA, and the current measured between the 11-th channel 2111, the area where the 11-th channel 2111 is attached, the area where the 12-th channel 2112 is attached, and the 12-th channel 2112 is 0.01 to 0.03 mA, or 0.45 mA or higher.

Here, if it is confirmed that the impedance exceeds the reference impedance, it may be assumed that an attachment defect is generated in the 11-th channel 2111, the 12-th channel 2112, the 21-th channel 2121 or the 22-th channel 2122, and thereafter, the stimulation signal module 2200 stops supply of the electric pulse signal of the adjusted magnitude of the absolute value.

Meanwhile, when the current measured between the 11-th channel 2111, the area where the 11-th channel 2111 is attached, the area where the 12-th channel 2112 is attached, and the 12-th channel 2112 is higher than the threshold value, the current measured between the 21-th channel 2121, the area where the 21-th channel 2121 is attached, the area where the 22-th channel 2122 is attached, and the 22-th channel 2122 is higher than the threshold value, and any one of the current measured between the 11-th channel 2111, the area where the 11-th channel 2111 is attached, the area where the 12-th channel 2112 is attached, and the 12-th channel 2112 and the current measured between the 21-th channel 2121, the area where the 21-th channel 2121 is attached, the area where the 22-th channel 2122 is attached, and the 22-th channel 2122 is lower than 1.5 times of the other, it is confirmed that the impedance does not exceed the reference impedance, and the stimulation signal module 2200 provides the 11-th channel 2111, the 12-channel 2112, the 21-th channel 2121 and the 22-th channel 2122 with an electric pulse signal of the adjusted magnitude of the absolute value.

Hereinafter, an experiment result of treating damaged corneal nerves using a method of using a multichannel stimulation system for regenerating damaged corneal nerves according to the embodiments of the present invention will be described with reference to FIGS. 13 and 14.

Figure 13:
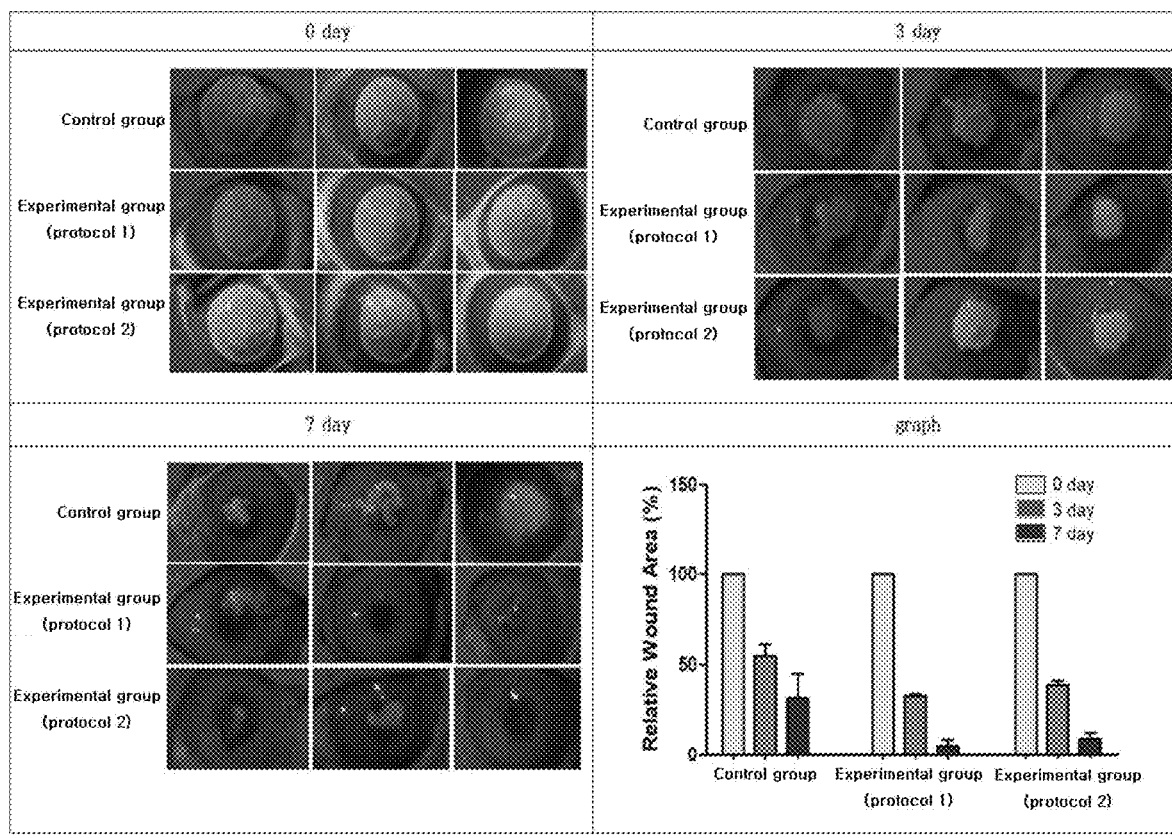
FIG. 13 is a view showing pictures of measuring a degree of treatment of epithelial cells of a damaged cornea after 0 days, 3 days, and 7 days are elapsed while treating the damaged cornea using a method of using a multichannel stimulation system for regenerating damaged corneal nerves according to an embodiment of the present invention.

FIG. 13 is a view showing pictures of measuring a degree of treatment of epithelial cells of a damaged cornea after 0 days, 3 days, and 7 days are elapsed while treating the damaged cornea using a method of using a multichannel stimulation system for regenerating damaged corneal nerves according to an embodiment of the present invention. Here, a control group measures a damaged cornea of a patient, who has undergone vision correction surgery of cutting part of the cornea, after the patient has a normal treatment for the cornea (e.g., antibiotic administration), first protocol experimental group measures the damaged cornea while treating the damaged cornea nerves with an electric pulse signal of 20 Hz using a method of using a multichannel stimulation system for regenerating damaged cornea nerves according to the embodiments of the present invention, in addition to the normal treatment (e.g., antibiotic administration for the cornea of a patient who has undergone vision correction surgery of cutting part of the cornea, and second protocol experimental group measures the damaged cornea while treating the damaged cornea nerves with an electric pulse signal of 2 Hz using a method of using a multichannel stimulation system for regenerating damaged cornea nerves according to the embodiments of the present invention, in addition to the normal treatment (e.g., antibiotic administration) for the cornea of the patient who has undergone vision correction surgery of cutting part of the cornea.

As shown in FIG. 13, during the 0-th day, there is no difference between the control group, the first experimental group and the second experimental group, and after three days are elapsed, 54% of the relative damaged area of the control group remain, 32% of the relative damaged area of the first protocol experimental group remain, and 39% of the relative damaged area of the second protocol experimental group remain.

Meanwhile, after seven days are elapsed, 31% of the relative damaged area of the control group remain, 4.7% of the relative damaged area of the first protocol experimental group remain, and 9.0% of the relative damaged area of the second protocol experimental group remain.

Figure 14:
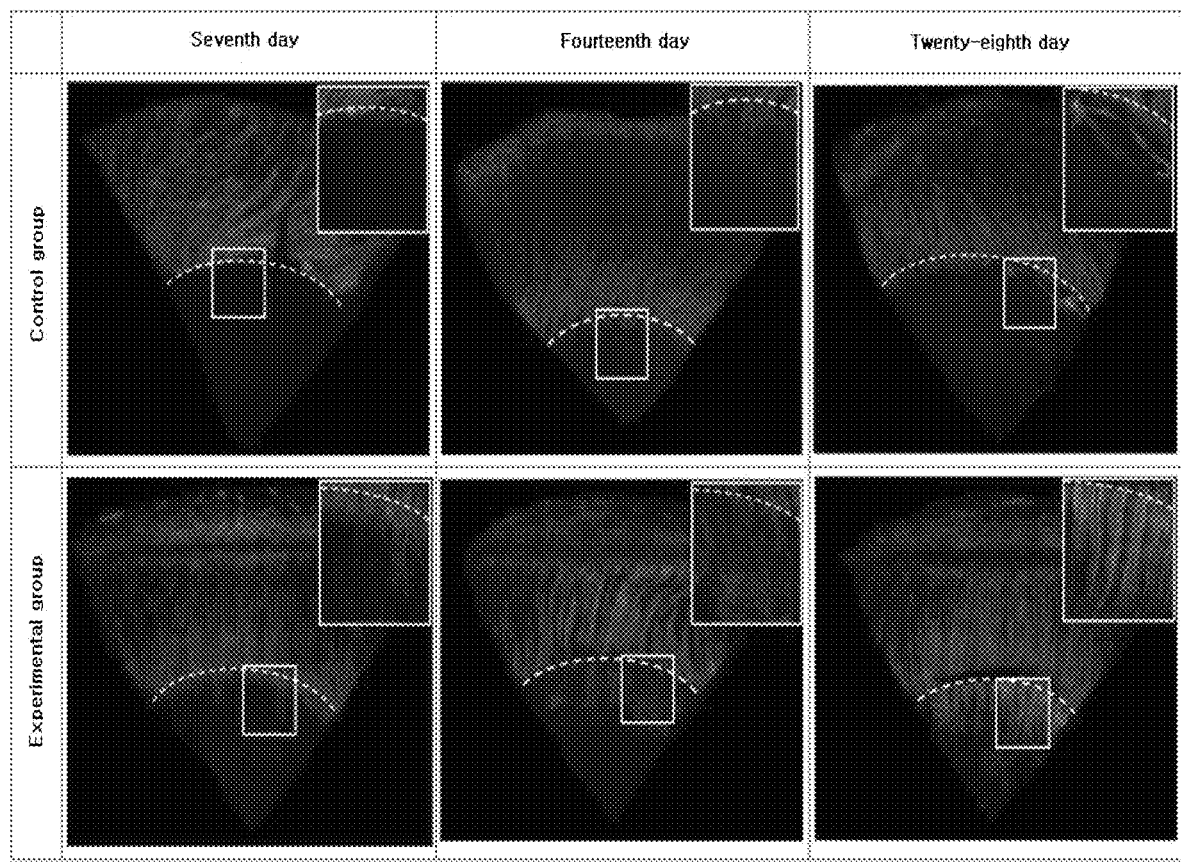
FIG. 14 is a view showing pictures of measuring a degree of regeneration of nerve cells of a damaged cornea using a confocal microscope after 1 week, 2 weeks, and 4 weeks are elapsed while treating the damaged cornea using a method of using a multichannel stimulation system for regenerating damaged corneal nerves according to an embodiment of the present invention.

FIG. 14 is a view showing pictures of measuring a degree of regeneration of nerve cells of a damaged cornea using a confocal microscope after 1 week, 2 weeks, and 4 weeks are elapsed while treating the damaged cornea using a method of using a multichannel stimulation system for regenerating damaged corneal nerves according to an embodiment of the present invention. Here, a control group measures a degree of regeneration of the nerve cells of a damaged cornea of a patient, who has undergone vision correction surgery of cutting part of the cornea, after the patient has a normal treatment (e.g., antibiotic administration) for the cornea, and an experimental group measures a degree of regeneration of the nerve cells of the damaged cornea while treating the damaged cornea nerves using a method of using a multichannel stimulation system for regenerating damaged corneal nerves according to the embodiments of the present invention, in addition to the normal treatment antibiotic administration) for the cornea of the patient who has undergone vision correction surgery of cutting part of the cornea.

As shown in FIG. 14, it is understood that the nerve cells of the damaged cornea are regenerated more actively in the experimental groups, compared with the control group, as time is elapsed more.

The method of using a multichannel stimulation system for regenerating damaged corneal nerves according to the embodiments of the present invention may effectively transfer an electric pulse signal into multiple channel attaching areas by applying the electric pulse signal as a stimulation signal through multiple channels attached in a plurality of areas close to the eyes, and measuring impedance between the multiple channels and the multiple channel attaching areas.

Although the present invention has been described and shown in relation to the preferred embodiments for illustrating the principle of the present invention, the present invention is not limited to the configuration and operation as is shown and described.

Rather, those skilled in the art may fully understand that the present invention can be diversely changed and modified without departing from the spirit and scope of the appended claims.

Accordingly, all proper changes, modifications and equivalents should be regarded as being included in the scope of the present invention.

What is claimed is:

1. A method of using a multichannel stimulation system for regenerating damaged corneal nerves, the system comprising
   a multichannel unit including a first channel formed of a conductive material and configured to be attached between an area above a left eye and a left eyebrow to transfer a stimulation signal, and a second channel formed of a conductive material, configured to be attached between an area above a right eye and a right eyebrow to transfer the stimulation signal, and formed in one piece together with the first channel; and a stimulation signal module for providing the first channel and the second channel with an electric pulse signal as the stimulation signal, and the method comprising the steps of:

providing the electric pulse signal configured of a positive current pulse signal during a first duration time, a zero current electric pulse signal during a second duration time following the first duration time, a negative current pulse signal during a third duration time following the second duration time, a zero current electric pulse signal during a fourth duration time following the third duration time, a negative current pulse signal during a fifth duration time following, the fourth duration time, a zero current electric pulse signal during a sixth duration time following the fifth duration time, a positive current pulse signal during a seventh duration time following the sixth duration time, and a zero current electric pulse signal during an eighth duration time following the seventh duration time, by the stimulation signal module;

transferring the electric pulse signal of the first duration time and the electric pulse signal of the seventh duration time to the first channel, and transferring the electric pulse signal of the third duration time and the electric pulse signal of the fifth duration time to the second channel, by the stimulation signal module;

maintaining an adjusted magnitude of an absolute value of the electric pulse signal, when the adjusted magnitude of the absolute value of the electric pulse signal desired by a user is adjusted by controlling to increase the adjusted magnitude of the absolute value of the electric pulse signal in proportion to the number of times of applying a pressure to an up button of the stimulation signal module and controlling to decrease the adjusted magnitude of the absolute value of the electric pulse signal in inverse proportion to the number of times of applying a pressure to a down button of the stimulation signal module; and measuring impedance between the first channel and an area where the first channel is configured to be attached and impedance between the second channel and an area where the second channel is configured to be attached, and confirming whether the impedance measured between the first channel and the area where the first channel is configured to be attached and the impedance measured between the second channel and the area where the second channel is configured to be attached exceed a reference impedance, wherein a length of the first duration time of the electric pulse signal is 2 to 15 times of a length of the third duration time of the electric pulse signal, and a length of the fifth duration time of the electric pulse signal is 2 to 15 times of a length of the seventh duration time of the electric pulse signal.

2. The method according to claim 1, wherein at the step of confirming whether the reference impedance is exceeded, the stimulation signal module applies a DC voltage of a predetermined magnitude to the first channel, measures a current between the first channel, the area where the first channel is configured to be attached, the area where the second channel is configured to be attached, and the second channel, and confirms that the impedance exceeds the reference impedance when the measured current is lower than a threshold value.

3. The method according to claim 2, wherein at the step of confirming whether the reference impedance is exceeded, if it is confirmed that the impedance exceeds the reference impedance, the stimulation signal module stops supply of the electric pulse signal of the adjusted magnitude of the absolute value.

4. The method according to claim 2, wherein at the step of confirming whether the reference impedance is exceeded, if it is confirmed that the current measured between the first channel, the area where the first channel is configured to be attached, the area where the second channel is configured to be attached, and the second channel is higher than the threshold value and thus the impedance does not exceed the reference impedance, the stimulation signal module provides the first channel and the second channel with an electric pulse signal of the adjusted magnitude of the absolute value.

5. The method according to claim 1, wherein magnitude of an absolute value of the positive current electric pulse signal of the first duration time of the electric pulse signal is equal to magnitude of an absolute value of the negative current electric pulse signal of the third duration time of the electric pulse signal, and magnitude of an absolute value of the negative current electric pulse signal of the fifth duration time of the electric pulse signal is equal to magnitude of an absolute value of the positive current electric pulse signal of the seventh duration time of the electric pulse signal.

6. The method according to claim 1, wherein magnitude of an absolute value of the positive current electric pulse signal of the first duration time of the electric pulse signal is 2 to 15 times of magnitude of an absolute value of the negative current electric pulse signal of the third duration time of the electric pulse signal, and magnitude of an absolute value of the negative current electric pulse signal of the fifth duration time of the electric pulse signal is 2 to 15 times of magnitude of an absolute value of the positive current electric pulse signal of the seventh duration time of the electric pulse signal.

7. The method according, to claim 6, wherein the electric pulse signal is in a charge-balanced state.

8. The method according to claim 1, wherein the electric pulse signal is in a charge-balanced state.

9. A method of using a multichannel stimulation system for regenerating damaged corneal nerves, the system comprising:

a multichannel unit including a 11-th channel formed of a conductive material and configured to be attached above a left eyebrow to transfer a stimulation signal, a 12-th channel formed of a conductive material and configured to be attached below a left eye to transfer the stimulation signal, a 21-th channel formed of a conductive material and configured to be attached above a right eyebrow to transfer the stimulation signal, and a 22-th channel formed of a conductive material, configured to be attached below a right eye to transfer the stimulation signal, and formed in one piece together with the 11-th channel, the 12-th channel and the 21-th channel; and a stimulation signal module for providing the 11-th channel, the 12-th channel, the 21-th channel and the 22-th channel with an electric pulse signal as the stimulation signal, and the method comprising the steps of:

providing the electric pulse signal configured of a positive current pulse signal during a first duration time, a zero current electric pulse signal during a second duration time following the first duration time, a negative current pulse signal during a third duration time following the second duration time, a zero current electric pulse signal during a fourth duration time following the third duration, time, a negative current pulse signal during a fifth duration time following the fourth duration time, a zero current electric pulse signal during a sixth duration time following the fifth duration time, a positive current pulse signal during a seventh duration time following the sixth duration time, and a zero current electric pulse signal during an eighth duration time following the seventh duration time, by the stimulation signal module;

transferring the electric pulse signal of the first duration time and the electric pulse signal of the seventh duration time to the 11-th channel, transferring the electric pulse signal of the third duration time and the electric pulse signal of the fifth duration time to the 12-th channel, transferring the electric pulse signal of the first duration time and the electric pulse signal of the seventh duration time to the 21-th channel, and transferring the electric pulse signal of the third duration time and the electric pulse signal of the fifth duration time to the 22-th channel, by the stimulation signal module;

maintaining an adjusted magnitude of an absolute value of the electric pulse signal when the adjusted magnitude of the absolute value of the electric pulse signal desired by a user is adjusted by controlling to increase the adjusted magnitude of the absolute value of the electric pulse signal in proportion to the number of times of applying a pressure to an up button of the stimulation signal module and controlling to decrease the adjusted magnitude of the absolute value of the electric pulse signal in inverse proportion to the number of times of applying a pressure to a down button of the stimulation signal module, and measuring impedance between the 11-th channel and an area where the 11-th channel is configured to be attached and impedance between the 12-th channel and an area where the 12-th channel is configured to be attached, measuring impedance between the 21-th channel and an area where the 21-th channel is configured to be attached and impedance between the 22-th channel and an area where the 22-th channel is configured to be attached, confirming whether the impedance measured between the 11-th channel and the area where the 11-th channel is configured to be attached and the impedance measured between the 12-th channel and the area where the 12-th channel is configured to be attached exceed a reference impedance, and confirming whether the impedance measured between the 21-th channel and the area where the 21-th channel is configured to be attached and the impedance measured between the 22-th channel and the area where the 22-th channel is configured to be attached exceed a reference impedance, wherein a length of the first duration time of the electric pulse signal is 2 to 15 times of a length of the third duration time of the electric pulse signal, and a length of the fifth duration time of the electric pulse signal is 2 to 15 times of a length of the seventh duration time of the electric pulse signal.

10. The method according to claim 9, wherein at the step of confirming whether the reference impedance is exceeded, when the stimulation signal module applies a DC voltage of a predetermined magnitude to the 11-th channel and measures a current between the 11-th channel, the area where the 11-th channel is configured to be attached, the area where the 12-th channel is configured to be, attached, and the 12-th channel, and the measured current is lower than a threshold value, or when the stimulation signal module applies a DC voltage of a predetermined magnitude to the 21-th channel and measures a current between the 21-th channel, the area where the 21-th channel is configured to be attached, the area where the 22-th channel is configured to be attached, and the 22-th channel, and the measured current is lower than the threshold value, it is confirmed that the impedance exceeds the reference impedance, and when the current measured between the 11-th channel, the area where the 11-th channel is configured to be attached, the area where the 12-th channel is configured to be attached, and the 12-th channel is higher than the threshold value, the current measured between the 21-th channel, the area where the 21-th channel is configured to be attached, the area where the 22-th channel is configured to be attached, and the 22-th channel is higher than the threshold value, and any one of the current measured between the 11-th channel, the area where the 11-th channel is configured to be attached, the area where the 12-th channel is configured to be attached, and the 12-th channel and the current measured between the 21-th channel, the area where the 21-th channel is configured to be attached, the area where the 22-th channel is configured to be attached, and the 22-th channel is equal to or higher than 1.5 times of the other, it is confirmed that the impedance exceeds the reference impedance.

11. The method according to claim 10, wherein at the step of confirming whether the reference impedance is exceeded, if it is confirmed that the impedance exceeds the reference impedance, the stimulation signal module stops supply of the electric pulse signal of the adjusted magnitude of the absolute value.

12. The method according to claim 10, wherein at the step of confirming whether the reference impedance is exceeded, when the current measured between the 11-th channel, the area where the 11-th channel is configured to be attached, the area where the 12-th channel is configured to be attached, and the 12-th channel is higher than the threshold value, the current measured between the 21-th channel, the area where the 21-th channel is configured to be attached, the area where the 22-th channel is configured to be attached, and the 22-th channel is higher than the threshold value, and any one of the current measured between the 11-th channel, the area where the 11-th channel is configured to be attached, the area where the 12-th channel is configured to be attached, and the 12-th channel and the current measured between the 21-th channel, the area where the 21-th channel is configured to be attached, the area where the 22-th channel is configured to be attached, and the 22-th channel is lower than 1.5 times of the other, it is confirmed that the impedance does not exceed the reference impedance, and the stimulation signal module provides the 11-th channel, the 12-channel, the 21-th channel and the 22-th channel with an electric pulse signal of the adjusted magnitude of the absolute value.

13. The method according to claim 9, wherein magnitude of an absolute value of the positive current electric pulse signal of the first duration time of the electric pulse signal is equal to magnitude of an absolute value of the negative current electric pulse signal of the third duration time of the electric pulse signal, and magnitude of an absolute value of the negative current electric pulse signal of the fifth duration time of the electric pulse signal is equal to magnitude of an absolute value of the positive current electric pulse signal of the seventh duration time of the electric pulse signal.

14. The method according to claim 9, wherein magnitude of an absolute value of the positive current electric pulse signal of the first duration time of the electric pulse signal is 2 to 15 times of magnitude of an absolute value of the negative current electric pulse signal of the third duration time of the electric pulse signal, and magnitude of an absolute value of the negative current electric pulse signal of the fifth duration time of the electric pulse signal is 2 to 15 times of magnitude of an absolute value of the positive current electric pulse signal of the seventh duration time of the electric pulse signal.

15. The method according to claim 14, wherein the electric pulse signal is in a charge-balanced state.

16. The method according to claim 9, wherein the electric pulse signal is in a charge-balanced state.

\* \* \* \* \*